(12) United States Patent
Sharp et al.

(10) Patent No.: US 6,457,974 B1
(45) Date of Patent: Oct. 1, 2002

(54) INTRAORAL DENTAL ABRADING INSTRUMENT

(75) Inventors: Michael C. Sharp, Centerport, NY (US); Kevin Klocek, Boise, ID (US); Stuart A. Mitchell, Harwinton, CT (US)

(73) Assignee: Parkell, Inc., Farmingdale, NY (US)

( * ) Notice: Subject to any disclaimer, the term of this patent is extended or adjusted under 35 U.S.C. 154(b) by 0 days.

(21) Appl. No.: 09/442,975

(22) Filed: Nov. 18, 1999

(51) Int. Cl.$^7$ .................................................. A61C 3/02
(52) U.S. Cl. ........................................................ 433/88
(58) Field of Search ................................ 433/80, 88, 84

(56) References Cited

U.S. PATENT DOCUMENTS

| | | | |
|---|---|---|---|
| 1,398,527 A | | 11/1921 | Muspratt |
| 2,661,537 A | | 12/1953 | Angell |
| 2,744,361 A | | 5/1956 | Larson |
| 3,164,513 A | * | 1/1965 | Zorzi |
| 3,421,702 A | | 1/1969 | O'Brien |
| 3,894,338 A | * | 7/1975 | Loge et al. |
| 3,905,554 A | | 9/1975 | Bell |
| 3,972,123 A | | 8/1976 | Black |
| 4,174,571 A | | 11/1979 | Gallant |
| 4,260,382 A | * | 4/1981 | Thomson ..................... 433/126 |
| 4,403,956 A | * | 9/1983 | Nakanishi ..................... 433/29 |
| 4,412,402 A | | 11/1983 | Gallant |
| 4,522,597 A | | 6/1985 | Gallant |
| 4,540,365 A | | 9/1985 | Nelson |
| 4,595,365 A | | 6/1986 | Edel et al. |
| 4,608,018 A | * | 8/1986 | Ghedini et al. ................ 433/88 |
| 4,648,840 A | | 3/1987 | Conger, Sr. |
| 4,776,794 A | | 10/1988 | Meller |
| 4,941,298 A | | 7/1990 | Fernwood |
| 4,950,160 A | * | 8/1990 | Karst ............................ 433/88 |
| 5,199,229 A | | 4/1993 | Herold |
| 5,234,338 A | | 8/1993 | Young |
| 5,252,064 A | * | 10/1993 | Baum et al. ................... 433/80 |
| 5,658,144 A | * | 8/1997 | Tinder et al. |
| 5,746,596 A | | 5/1998 | Gallant |
| 5,765,759 A | * | 6/1998 | Bruns et al. .................. 239/398 |
| 5,941,702 A | * | 8/1999 | Sharp et al. .................... 433/88 |
| 6,106,287 A | * | 8/2000 | Yates ............................ 433/82 |

FOREIGN PATENT DOCUMENTS

| | | |
|---|---|---|
| DE | 3101632 C2 | 8/1982 |
| DE | 3242306 C2 | 5/1984 |
| DE | G8808484.9 | 10/1988 |
| DE | 3841069 A1 | 8/1989 |
| EP | 0225193 B | 6/1987 |
| WO | WO 91/03640 | 3/1991 |

OTHER PUBLICATIONS

Brochure pages from Electro Medical Systems for Air–Flow system, dated Mar. 1999, Germany.

* cited by examiner

*Primary Examiner*—Ralph A. Lewis
(74) *Attorney, Agent, or Firm*—Daniel R. Schechter

(57) ABSTRACT

A hand-held dental instrument for intraoral abrading of teeth includes a light-weight body made from a high temperature material and having internal bores or passageways for permitting fluid flow through the body. A rotatable nozzle assembly having internal fluid conduits therein is coupled to a distal end of the body such that a chamber is formed between the nozzle and the body. The chamber maintains fluid communication between an internal bore which is radially offset from a central axis bore of the body and an internal conduit of the nozzle assembly such that the nozzle can be rotated a full 360 degrees with respect to the body. The nozzle assembly includes a primary discharge port for directing flow of the air/abrasive material mixture and a secondary discharge port for directing a stream of liquid to a surface to be abraded. The primary discharge port of the nozzle head is preferably larger in diameter than the secondary discharge port and is disposed at an angle with respect to the secondary discharge port to meet at a point forward of the nozzle head. The handpiece is also provided with its own self-contained abrasive material supply which may be connected to the body or may be contained within the body. The abrasive material supply includes a coaxial pick-up tube and canister.

1 Claim, 7 Drawing Sheets

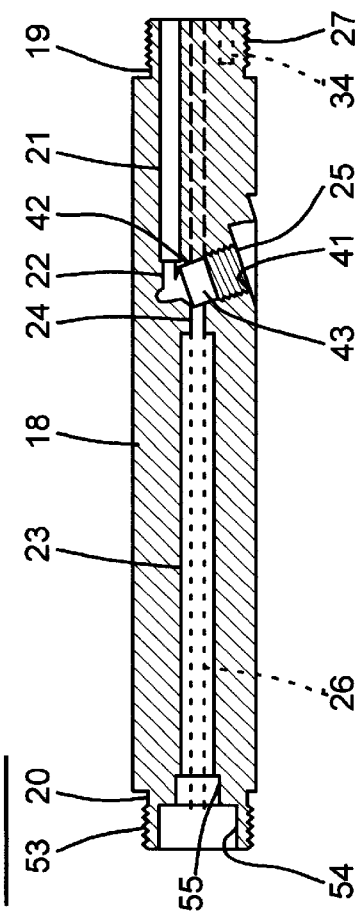
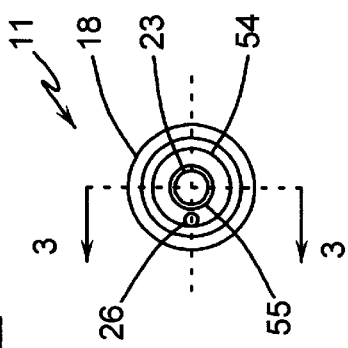
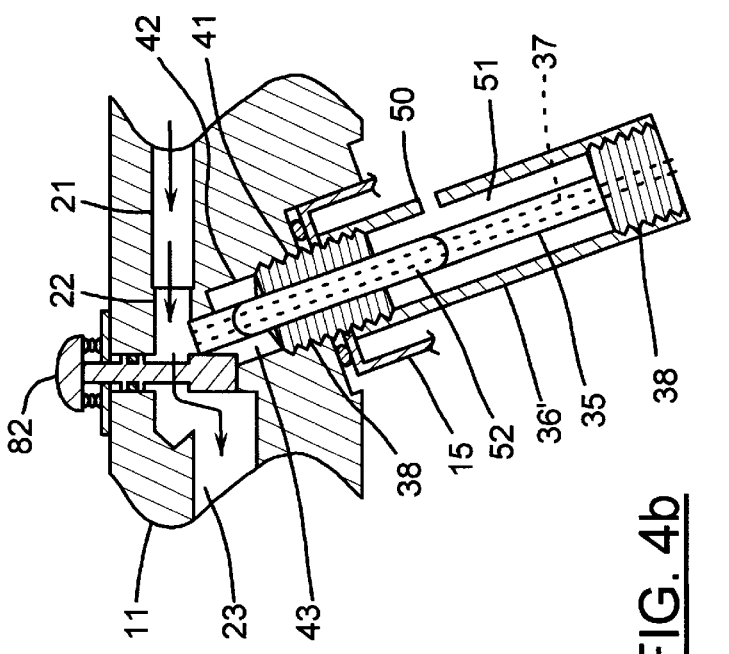
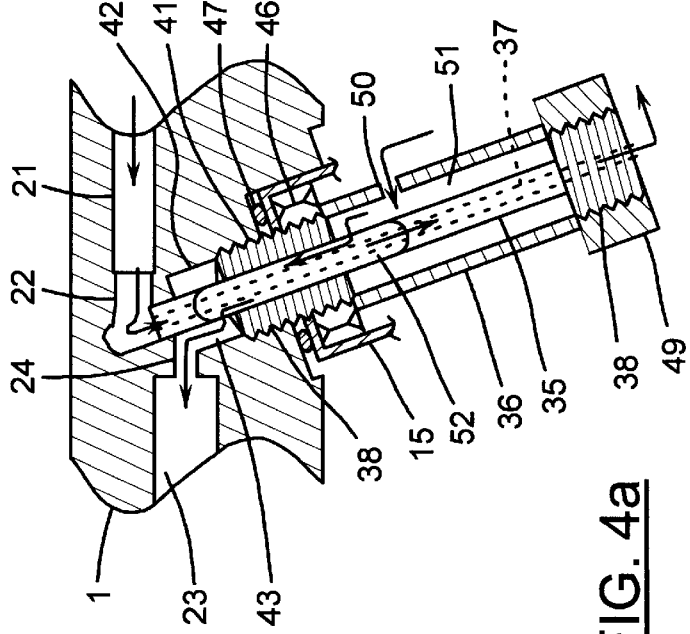

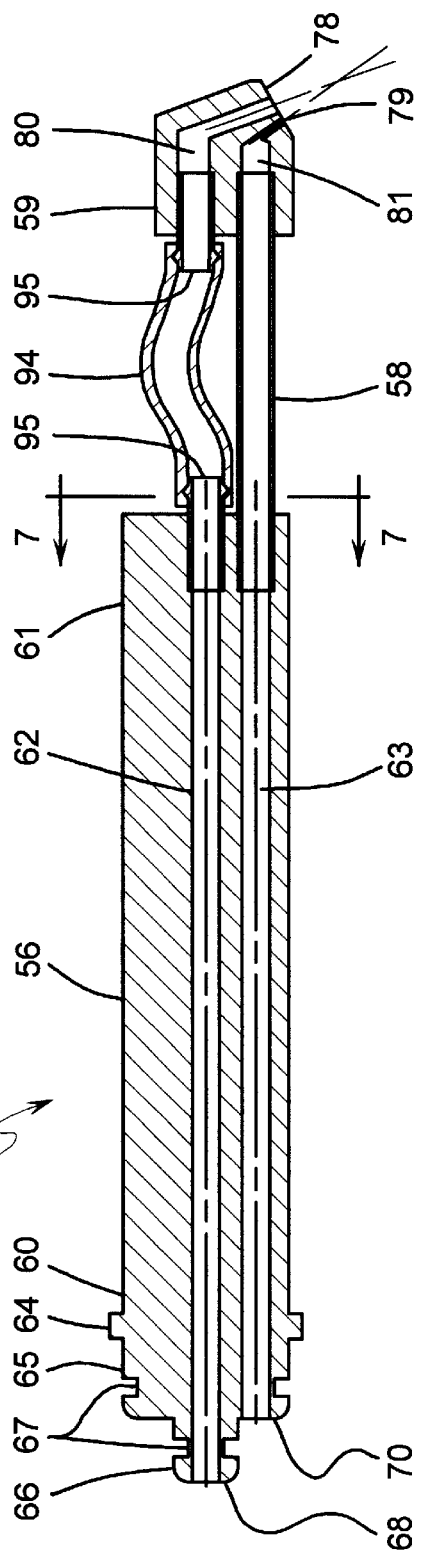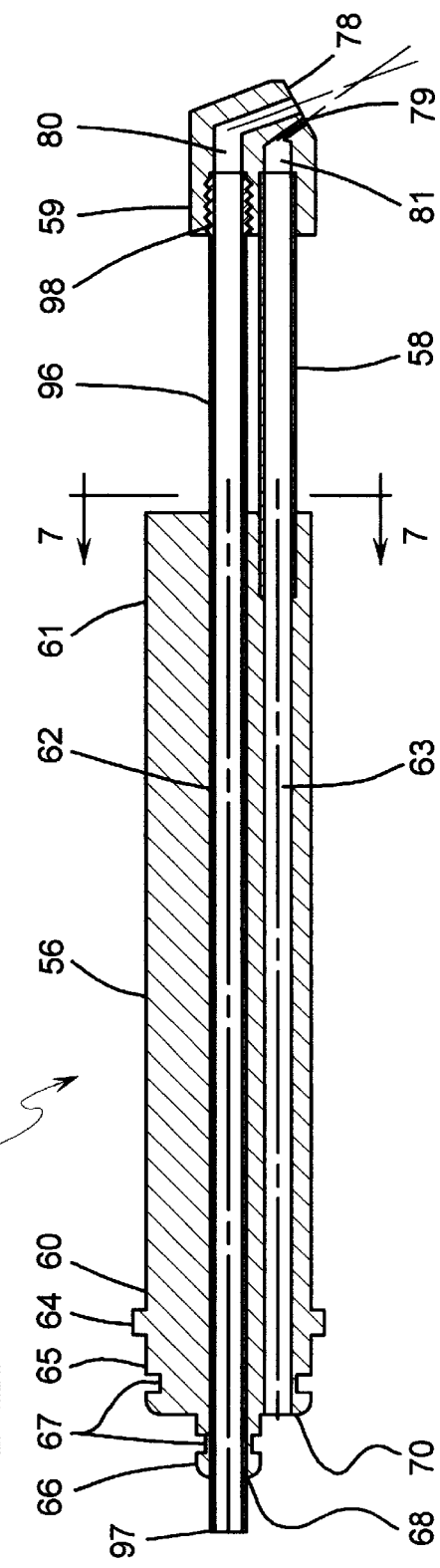

INTRAORAL DENTAL ABRADING INSTRUMENT

BACKGROUND OF THE INVENTION

1. Field of the Invention

The present invention relates generally to a hand-held dental instrument for intraoral abrading of teeth.

2. Description of the Prior Art

Use of hand-held dental abrading tools utilizing a pressurized slurry of bicarbonate, water and air to clean, polish and/or remove biofilm and heavy stains on the teeth is well known in the dental industry. Such tools operate by directing a gaseous stream mixed with an abrasive material to the tooth surface to be cleaned. The gaseous medium, (often compressed air), and small solid particles comprising the abrasive material are supplied to the tool and are mixed so that the abrasive material becomes entrained within the gaseous medium. The mixture is then discharged through a nozzle upon activation of the tool by the operator. Water is also often provided to dissolve the abrasive material and wash it from the surface of the tooth being abraded. Water may be mixed with the abrasive material internally within the tool or a stream of water may be separately directed from the nozzle to the surface being cleaned. Unfortunately, most polishing tools are somewhat expensive, bulky, prone to clogging and/or are not sterilizable by autoclaving. Accordingly, it would be advantageous to provide a hand-held dental abrading instrument which is easy to manufacture, reliable in operation, easy to grasp and manipulate and fully sterilizable by autoclaving.

Objects and Summary of the Invention

It is an object of the present invention to provide a low-cost, easily manufactured dental abrading instrument which is easily grasped and manipulated within the confines of a patient's mouth.

It is another object of the present invention to provide a handpiece for a dental abrading instrument which is sterilizable by standard autoclaving techniques.

It is yet another object of the present invention to provide a dental abrading instrument having a fully rotatable nozzle which can be gripped comfortably between the thumb and forefinger of the user and which is easily removed and replaced by another similar nozzle when needed.

It is yet a further object of the present invention to provide a dental abrading instrument having a nozzle which provides optimal mixing of a pressurized abrasive stream with a water stream outside and forward of the tip of the nozzle to create a polishing slurry.

It is still another object of the present invention to provide a dental abrading instrument having a self-contained abrasive material supply having means for effectively entraining the abrasive material within a pressurized gaseous medium which is relatively simple and less prone to clogging.

It is still a further object of the present invention to provide a dental abrading instrument having its own light-weight flexible supply cord which is adapted to connect to any existing dental office air/water supply system.

The present invention is a low-cost, reliable compact dental abrading instrument which alleviates the above-mentioned drawbacks. Generally, the instrument includes a light-weight body made from a high temperature material and having internal passageways for permitting fluid flow through the body. A rotatable nozzle having internal fluid conduits therein is mounted on a distal end of the body such that a chamber is formed between the nozzle and the body. The chamber maintains fluid communication between the internal bores of the body and the internal conduits of the nozzle such that the nozzle can be rotated a full 360 degrees with respect to the body.

The body and the nozzle are formed with a coaxial arrangement of cooperative counterbores and barrel sections such that the chamber is defined by a space formed between the body and the nozzle. Preferably, the nozzle is provided with coaxial barrel portions which cooperate with counterbores formed in the body so that the chamber is defined by a space formed between a bottom surface of a larger outer counterbore and a top surface of a larger barrel section fitting therein. Alternatively, a single barrel portion may be provided on an interconnect face of the nozzle which fits within a smaller counterbore formed in the body so that the chamber is defined by a space formed between a bottom surface of a larger outer counterbore formed in the body and the interconnect face of the nozzle. In either embodiment, the body and the nozzle both include primary internal passageways which are axially aligned and in fluid communication with each other and further include secondary internal passageways which are each in fluid communication with the chamber. The primary passageways permit fluid flow of an air/abrasive material mixture and the secondary passageways permit fluid flow of a liquid stream.

The instrument is provided with a unique three-piece nozzle assembly comprising a nozzle grip having a plurality of internally formed passageways therein, a nozzle head having a plurality of discharge ports formed therein and a plurality of elongate extension tubes connecting the internal passageways of the nozzle grip to the discharge ports of the nozzle head. The nozzle arrangement includes a primary conduit terminating at a primary discharge port of the nozzle head for directing flow of the air/abrasive material mixture, and a secondary conduit terminating at a secondary discharge port of the nozzle head for directing a stream of liquid to a surface to be polished. The primary discharge port of the nozzle head is preferably larger in diameter than the secondary discharge port and is disposed at an angle with respect to the secondary discharge port so that the streams of the air/abrasive mixture and the liquid converge at a point a desired distance from the nozzle head discharge ports. In a preferred embodiment, the nozzle grip has a hexagonal cross-section for ease of manipulation. The nozzle assembly is easily removable from the body and may be replaced by another similar nozzle assembly so that the instrument can continue to be used while the previously used nozzle is being sterilized. Additionally, one or both of the elongate extension tubes may be made removable and separately sterilizable to permit enhanced internal cleaning of the nozzle components.

The instrument includes its own light-weight flexible supply line which is adapted to connect to any existing dental office air/water supply system. Differently designed adapters are provided to permit fluid communication between the body of the instrument, the respective conduits of the supply line and the air/ water supply system of the dental office. Depending on the dental office system, an appropriate adapter is selected and installed on the fluid supply line by the user thus permitting connection to any existing dental office air/water supply system.

The instrument also includes a self-contained abrasive material supply which may be connected to the body or which may form a part of the body itself. The supply may comprise an intake or pick-up tube, a cap and a canister which is connected to an abrasive material supply port of the body. The intake tube has a first end generally disposed within the canister and a second end cooperatively coupling the canister to the body. The intake tube is comprised of an inner sleeve, having a first fluid conduit formed therein, and an outer sleeve surrounding the inner sleeve and forming an annular fluid conduit between the inner and outer sleeves. Fluid enters the canister through the first conduit of the inner sleeve, agitates and becomes mixed with the abrasive material in the canister and exits the canister through the annular fluid conduit. The inner and outer sleeves are connected at the first end and the outer sleeve includes at least one opening through a wall thereof for fluidly connecting the canister chamber to the annular fluid outlet conduit.

Alternatively, the body of the instrument itself may form the abrasive material supply. In this embodiment, an abrasive material is contained within a chamber formed by a hollow portion of the body into which an inlet tube and an outlet tube extend. A gaseous fluid enters the chamber through the inlet tube, agitates and becomes mixed with the abrasive material in the chamber and exits the chamber through the outlet tube.

A preferred form of the handpiece, as well as other embodiments, objects, features and advantages of this invention will be apparent from the following detailed description of illustrative embodiments thereof which is to be read in conjunction with the accompanying drawings.

BRIEF DESCRIPTION OF THE DRAWINGS

FIG. 2 is a plan view of the distal end of the handpiece body of the dental polishing instrument of FIG. 1;

FIG. 3 is a longitudinal cross-sectional view of the body of FIG. 2 taken along the line 3—3;

FIG. 4a is a detailed view of the pick-up tube of the abrasive material supply connected to the handpiece body;

FIG. 4b is a detailed view of alternate embodiments of the pick-up tube and the abrasive material supply shown in FIG. 4;

FIG. 6b is a longitudinal cross-sectional view of an alternate embodiment of the nozzle assembly of FIG. 6a;

FIG. 6c is a longitudinal cross-sectional view of another alternate embodiment of the nozzle assembly of FIG. 6a;

DETAILED DESCRIPTION OF THE PREFERRED EMBODIMENTS

Figure 1:
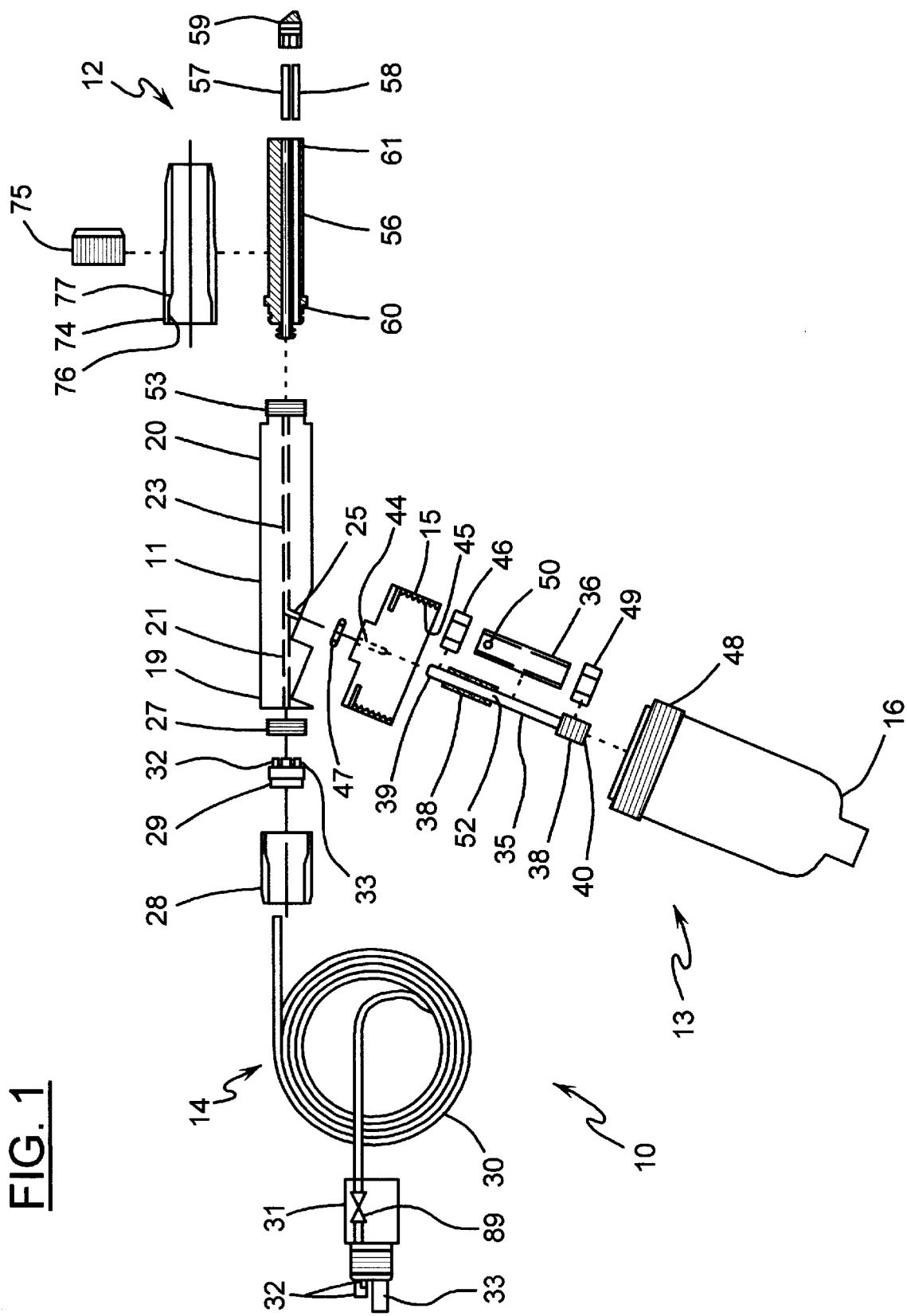
FIG. 1 is an exploded side view of the dental polishing instrument formed in accordance with the present invention.

Referring to FIG. 1, a preferred embodiment of an intraoral dental abrading instrument 10 formed in accordance with the present invention is shown. What is meant by an intraoral dental abrading instrument is any instrument used for polishing, cleaning and/or removing material from teeth. Generally, the dental abrading instrument 10 comprises an elongated body 11, a nozzle assembly 12, a supply of an abrasive material 13 and a fluid supply line 14.

Referring additionally to FIGS. 2 and 3, in the preferred embodiment, the body 11 is made from a suitable light-weight, solid autoclavable material and is preferably made from a plastic material such as Ultem® manufactured by General Electric Co., Plastics Group or Radel® manufactured by BP Amoco Group. A solid piece of titanium enclosed within an Ultem® or Radel® outer sleeve is another suitable material which may be used to form the body 11 to provide for long-lasting use. The solid body 11 has an outer surface 18, a proximal end 19, a distal end 20 and may be generally cylindrical in shape. Formed within the solid body 11 are a plurality of internal passageways extending from the proximal end 19 to the distal end 20. These passageways or bores may be formed using conventional machining techniques known in the art (e.g., drilling, reaming, electric discharge machining, etc.). An air inlet bore 21 begins at the proximal end 19 of the body 11 and terminates at a point 22 approximately one-third the distance of the length of the body 11. An abrasive mixture bore 23 extends within the body 11 generally along the body's central axis from the distal end 20 of the body and terminates at a point 24 which is generally coincident with the termination point 22 of the air inlet bore 21. An abrasive material connection port 25 extends radially inward from the outer surface 18 of the body and is in fluid communication with the air inlet bore 21 and the abrasive mixture bore 23. Preferably, the abrasive material connection port 25 is formed at an angle of approximately 60° to 70° relative to the outer surface 18 of the body which, as will be discussed in further detail below, facilitates comfortable gripping of the handpiece body. The solid body 12 further includes a bore 26 for carrying fluid which extends uninterrupted from the proximal end 19 to the distal end 20 of the handpiece body for permitting flow of a fluid, e.g. water, from the supply line 14 through the body 11. The center axis of the bore 26 for carrying fluid is radially displaced but substantially parallel to the center axis of the abrasive mixture bore 23.

The proximal end 19 of the body 11 includes an external thread 27 for connection to a mating connector 28 of the fluid supply line 14. The fluid supply line 14 includes the body connector 28, a body adaptor 29, a thin flexible hose 30 and a supply adapter 31. The hose 30 may include separate conduits for air and water formed therein or may be comprised of a pair of separate flexible tubes. The body adapter 29 permits fluid communication between the respective conduits or tubes of the hose 30 and the air inlet bore 21 and the water bore 26 of the body. The supply adapter 31 permits fluid communication between the respective conduits or tubes of the hose 30 and the air and water supply system of the dental office. The supply adapter 31 preferably includes check-valves 89 connected to the air and/or water lines to prevent backflow from the device into the air and/or water supplies, thus reducing the possibility of cross-contamination. The body adapter 29 may also be provided with a check-valve (not shown) which prevents backflow of water and/or air from the instrument body to the supply line 14. Both the body adapter 29 and the supply adapter 31 are provided with conventional barb fittings 32 for quick and easy connecting and disconnecting to the hose 30. The body adapter 29 is also provided with a guide pin 33 which fits within a mating guide hole 34 of the body 11 to provide proper alignment of the adapter with the body.

The fluid supply line 14 may be provided with any number of differently designed supply adapters each one configured to connect with a particular known dental office system. An appropriate supply adapter 31 is selected and installed on the fluid supply line 14 by the user depending on the air and water supply system of the particular dental office in which the instrument is to be used. In this manner, the light-weight and flexible fluid supply line 14 is adapted to connect to any existing dental office air/water supply system and the instrument 10 is activated by the same means, usually a foot pedal, as that for activating the supply system. Unlike conventional supply lines which are bulky and more rigid, the fluid supply line 14 according to the present invention utilizes a pair of thin, highly flexible, light-weight tubes to convey air and water directly from the dental office supply to the instrument allowing the user much greater freedom of movement with the instrument during procedures. Furthermore, there is no need for an additional intermediate control box or adapter connected between the instrument and the supply for activating the instrument as is required in many conventional dental abrasive systems.

Still referring to FIG. 1, in a preferred embodiment, the abrasive material supply 13 comprises a canister cap 15, an inner pick-up sleeve 35, an outer pick-up sleeve 36 and an abrasive material canister 16. Referring additionally to FIG. 4a, the inner pick-up sleeve 35 is generally a hollow cylindrical tube defining an internal fluid conduit 37 therein, and having externally threaded portions 38 formed on opposite first and second ends 39 and 40. The abrasive material connection port 25 formed in the body 11 includes an internal thread 41 which cooperatively engages the external thread 37 of the first end 39 of the inner pick-up sleeve 35. When the inner pick-up sleeve 35 is secured within the abrasive material connection port 25, the internal fluid conduit 37 of the inner pick-up sleeve 35 is in fluid communication with the air inlet bore 21 of the body 11. The abrasive material connection port 25 is also provided with a countersunk portion 42 which defines a chamber 43. The chamber 43 is in fluid communication with the abrasive mixture bore 23.

The canister cap 15 includes a central opening 44 through which the inner pick-up sleeve 35 protrudes and an internal thread 45 formed along the inner rim of the cap. A nut 46, which engages the external thread 38 of the first end 39 of the inner sleeve 35, is provide d to secure the cap 35 to the body 11. An O-ring 47 may be provided between the body 11 and the cap 15 to prevent leakage. The abrasive material canister 16 is provided with an external thread 48 formed at one end which engages the internal thread 45 of the canister cap 15 to secure the canister to the handpiece body 11. As mentioned earlier, for comfortable gripping of the handpiece body 11, the abrasive material supply 13 is preferably fixed to the body at an angle of approximately 60° to 70° relative to the body centerline. As such, the body 11 must be relieved in the area adjacent the abrasive material connection port 25 to accommodate the angular placement of the canister cap 15.

Once the canister cap 15 and the inner pick-up sleeve 35 are secured to the handpiece body, the outer pick-up sleeve 36 is inserted around the inner pick-up sleeve and secured to the inner pick-up sleeve by a nut 49 which engages the external thread 38 of the second end 40 of the inner sleeve. The outer pick-up sleeve 36 is also generally a hollow cylindrical tube having at least one radial through-hole 50 extending through the thickness of the cylindrical wall. The inner diameter of the outer pick-up sleeve 36 and the outer diameter of the unthreaded portion of the inner pick-up sleeve 35 are dimensioned such that they define an annular chamber 51 therebetween which is in fluid communication with the through-hole 50 of the outer pick-up sleeve, as shown in FIG. 4a. A keyway groove 52 is provided on the outer surface of the inner pick-up sleeve 35 which extends across the external thread 38 of the first end 39 of the inner pick-up sleeve to provide fluid communication between the annular chamber 51 and the abrasive material connection port chamber 43 of the handpiece body 11.

The abrasive material supply assembly 13 operates by providing pressurized air, as indicated by arrows in FIG. 4a, into the solid body 11 through the fluid supply line 14 and into the air inlet bore 21. Pressurized air from the air inlet bore 21 then enters the internal fluid conduit 37 of the inner pick-up sleeve 35 and flows into the abrasive material canister 16 where it agitates and mixes with an abrasive material stored therein. The abrasive material is preferably water soluble, such as bicarbonate. The abrasive material mixes and becomes entrained in the pressurized air stream within the canister. The abrasive material exits the canister 16 through the at least one through-hole 50 of the outer pick-up sleeve 36 and into the annular chamber 51 between the inner pick-up sleeve 35 and the outer pick-up sleeve 36. The abrasive material stream exits the annular chamber 51 via the keyway groove 52 and is forced into the internal chamber 43 of the abrasive material connection port 25. The air/abrasive mixture exits the connection port 25 and is provided to the abrasive mixture bore 23 of the handpiece body 11.

FIG. 4b shows several alternate embodiments for the abrasive material supply. The body 11 may include a bypass valve 82 which, when activated, blocks the internal chamber 43 of the abrasive material connection port 25 and allows the pressurized air from the air inlet bore 21 to bypass the abrasive material canister 16 and enter the abrasive mixture bore 23 without being mixed with the abrasive material. This allows the user to selectively apply abrasive material to the tooth surface and, if desired, rinse the mouth with the water/air mixture without any abrasive material in the stream. The bypass valve 82 shown in FIG. 4a is a spring biased push-button valve but could conceivably be a pressure activated valve, e.g., at lower pressures, which is controlled by the operator using a foot switch (not shown), the abrasive material canister is bypassed and at higher pressures of operation, the abrasive is provided to the handpiece nozzle.

An alternate embodiment for connection of the inner and outer pick-up sleeves is also shown in FIG. 4b. In this embodiment, the outer pick-up sleeve 36' is internally threaded at one end to connect with the external thread 38 of the second end 40 of the inner pick-up sleeve 35. The length of the outer pick-up sleeve 36' is sized such that when threaded on the inner pick-up sleeve 35 the end of the outer pick-up sleeve opposite the internally threaded end biases the canister cap 15 against the body 11. This allows the entire canister, including the cap, to be easily removed from the handpiece for easy cleaning and sterilization.

Figure 5A:
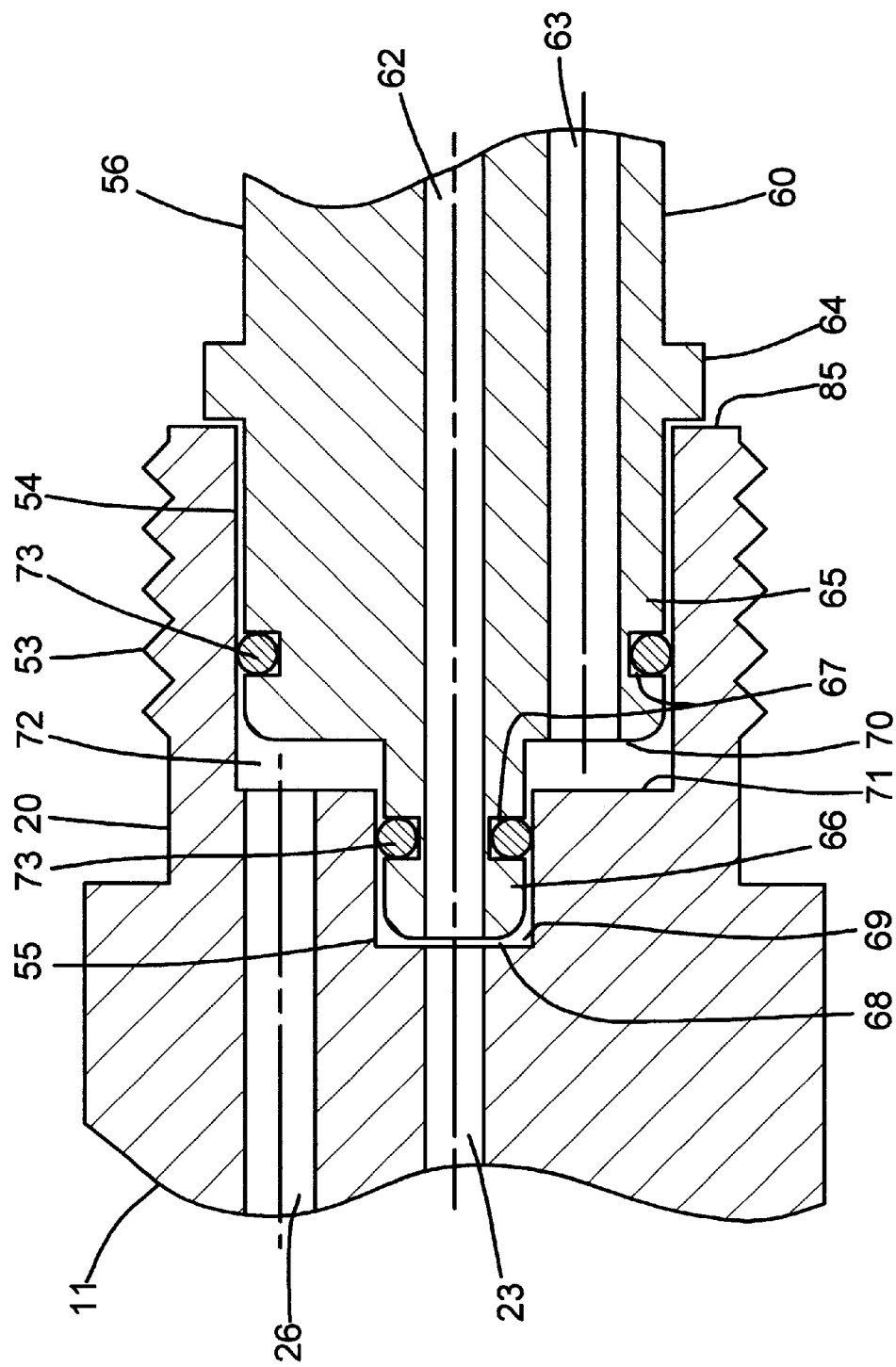
FIG. 5a is a detailed longitudinal cross-sectional view of the distal end of the body illustrating the rotatable nozzle assembly cooperatively coupled to the handpiece body.

Referring now to FIGS. 3 and 5a, the distal end 20 of the body 11 includes an external thread 53 and a pair of concentric circular counterbores 54 and 55 which, as will be discussed in further detail below, cooperate for connection to the nozzle assembly 12. A large counterbore 54 is formed on the distal end 20 of the body 11 generally concentric with the body's central axis. The diameter of the large counterbore 54 is dimensioned to permit fluid communication between the water bore 26 and the large counterbore. A smaller counterbore 55 is formed in the bottom wall 71 of the large counterbore 54 and is generally concentric with the large counterbore. The diameter of the smaller counterbore 55 is dimensioned so that the small counterbore is in fluid communication with only the centrally disposed abrasive mixture bore 23.

Figure 6A:
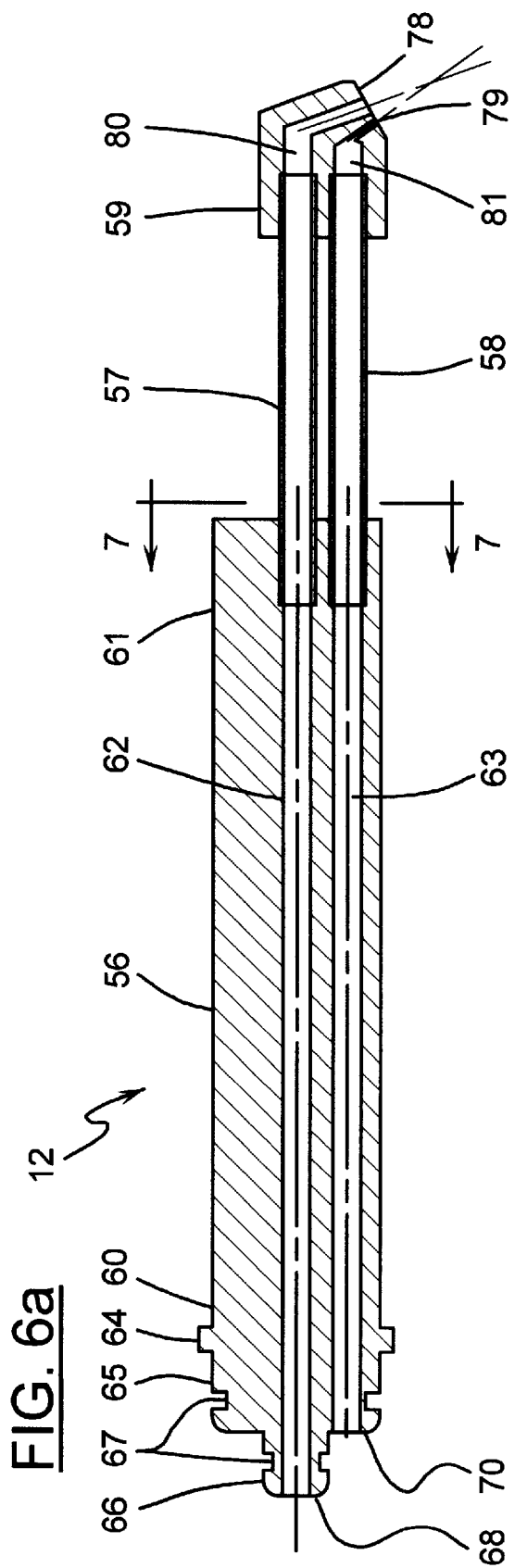
FIG. 6a is a longitudinal cross-sectional view of the nozzle assembly of FIG. 1.
Figure 7:
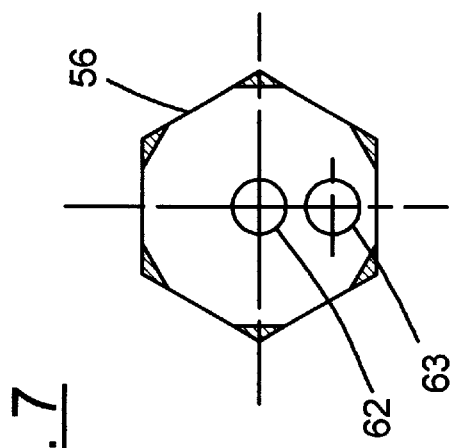
FIG. 7 is a view of the nozzle assembly of FIG. 6 taken along the line 7—7.

Referring additionally to FIGS. 6a and 7, disposed on the distal end 20 of the handpiece body 11 is a nozzle assembly 12 for directing the air/abrasive stream and the water stream from the body to the tooth surface to be cleaned. The nozzle assembly 12 generally includes a nozzle grip 56, a pair of extension tubes 57 and 58 and a nozzle head 59. The components of the nozzle assembly are preferably made from a stainless steel material, however, suitable hard solid plastics may also be used. The nozzle head 59 is preferably further hardened such as by conventional heat treating or other hardening techniques. The nozzle grip 56 is an elongate body preferably having a hexagonal shaped cross-section. It has been found that the hexagonal shape provides ease of manipulation between the thumb and forefinger of the user. The nozzle grip 56 includes an interconnect end 60 and a discharge end 61. Formed within the nozzle grip 56 and extending from the interconnect end 60 to the discharge end 61 are an abrasive mixture passageway 62 and a water passageway 63. The abrasive mixture passageway 62 is formed generally along the nozzle grip center line and the water passageway 63 is formed parallel to, but radially outward, from the nozzle grip center line.

The interconnect end 60 of the nozzle grip 56 includes a shoulder flange 64, a large cylindrical barrel section 65 formed rearward of the shoulder flange 64, and a smaller cylindrical barrel section 66 formed rearward of the large cylindrical barrel 65. The shoulder flange 64 provides a stop for inserting the nozzle assembly 12 into the handpiece body 11. The shoulder flange 64, the large barrel section 65 and the small barrel section 66 are all formed concentric with the centrally aligned abrasive material passageway 62. The barrel sections are formed such that the abrasive mixture passageway 62 terminates at the rearward face 68 of the small barrel section 66 and the water passageway 63 terminates at the rearward face 70 of the large barrel section 65. Additionally, the outer diameters of the large and small cylindrical barrels 65 and 66 are sized slightly smaller than the inner diameters of the large and small counterbores 54 and 55, respectively, formed in the distal end 20 of the body 11, as detailed in FIG. 5 to allow the O-rings 73 to prevent leakage. Formed on the outer surfaces of the large and small cylindrical barrels 65 and 66 respectively, are annular O-ring grooves 67 which receive correspondingly sized O-rings 73. The O-rings 73 along with the close fitting relationship between the barrel sections and the counterbores prevent leakage between the fluid passageways 26 and 63 and the air/abrasive passageways 23 and 62 at the interface between the handpiece body 11 and the nozzle assembly 12.

Referring specifically to FIG. 5a, the length of the large cylindrical barrel 65 is such that when the nozzle assembly 12 is positioned within the solid body 11 and the shoulder flange 64 engages an end face 85 of the body 11, the rearward face 70 of the large barrel section 65 is positioned a distance spaced away from the bottom wall 71 of the large counterbore 54. The gap or space formed between the rearward face 70 of the large cylindrical barrel 66 and the bottom wall 71 of large counterbore 54 defines a chamber 72 within the solid body 11 when the nozzle grip 56 is inserted within the distal end 20 of the body. The chamber 72 provides fluid communication between the water bore 26 of the body 11 and the water passageway 63 of the nozzle grip 56. The central alignment of the abrasive mixture bore 23 of the body 11 and the abrasive mixture passageway 62 of the nozzle grip 56 also provides fluid communication therebetween. The chamber 72 permits the nozzle grip to be rotated 360° while maintaining fluid communication between the water bore 26 of the body and the water passageway 63 of the grip regardless of orientation of the bores 26 and 63.

Figure 5B:
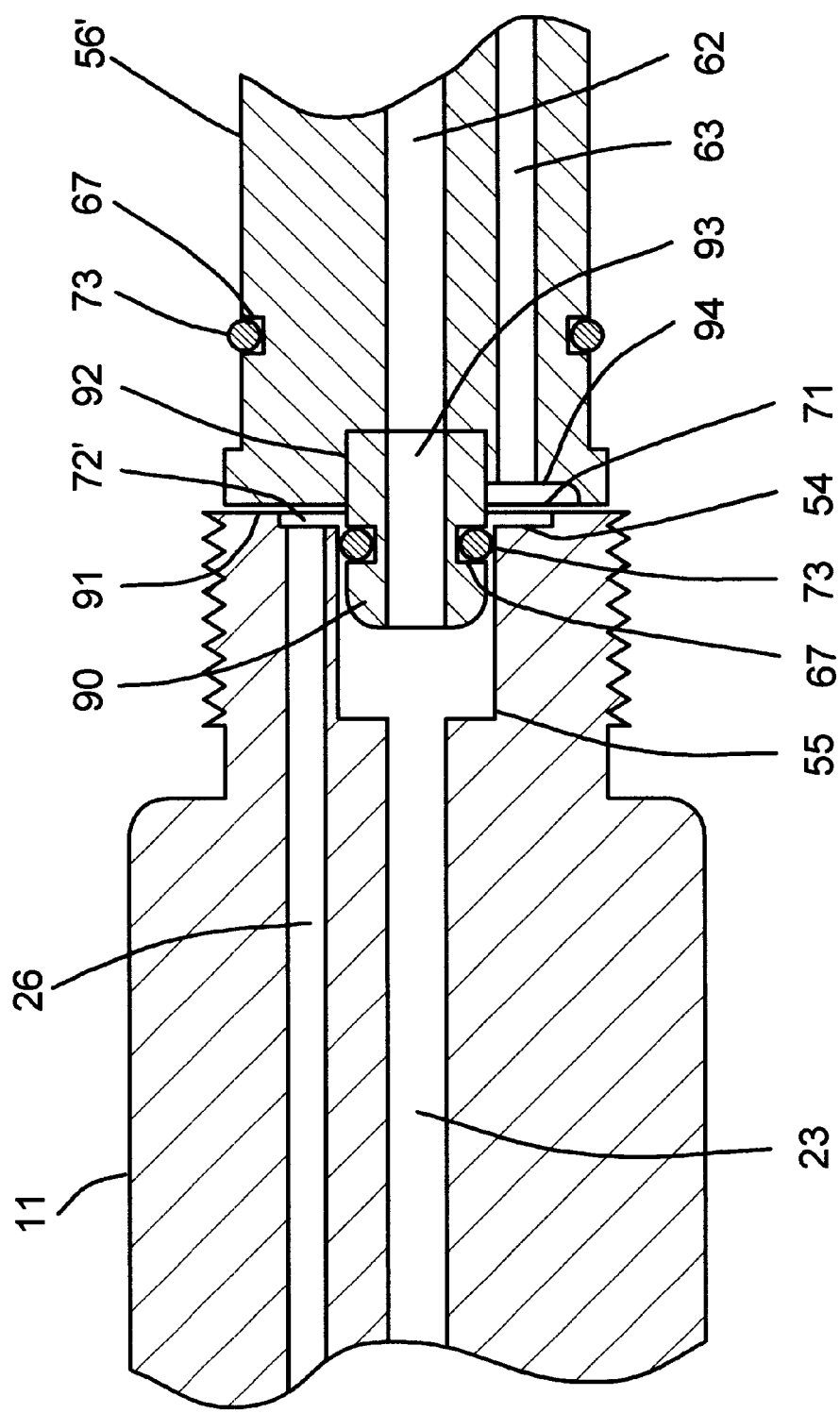
FIG. 5b is a detailed longitudinal cross-sectional view of the distal end of the body illustrating the rotatable nozzle assembly cooperatively coupled to the handpiece body in an alternate embodiment.

In an alternate embodiment, as shown in FIG. 5b, a single barrel portion 90 may be provided on an interconnect face 91 of a nozzle grip 56' which fits within the smaller counterbore 55 of the body 11. The single barrel portion 90 may take the form of a pin which is press-fit into a hole 92 formed centrally in the interconnect face 91, as shown in FIG. 5b, or may be formed on the interconnect face integrally with the nozzle grip 56'. The single barrel portion 90 includes a central bore 93 which permits fluid communication between the abrasive mixture passageway 62 of the nozzle grip 56' and the abrasive mixture bore 23 of the body 11 when the single barrel portion is inserted in the small counterbore 55 of the body. The single barrel portion 90 is also provided with an annular O-ring groove 67 which receives a correspondingly sized O-ring 73 to prevent leakage.

In this embodiment, a fluid communication chamber 72' is defined by the space formed between the bottom wall 71 of the large counterbore 54 of the body 11 and the interconnect face 91 of the nozzle grip 56' for permitting fluid communication between the water bore 26 of the body and the water passageway 63 of the nozzle grip 56' regardless of the orientation of the bore 26 and the passageway 63. The body 11 is formed as described above with the exception that, in the absence of the large barrel section 65, the depth of the large counterbore 54 is not as critical so long as fluid communication between the water bore 26 of the body and the water passageway 63 of the nozzle grip is maintained throughout 360° rotation of the nozzle grip. To enhance fluid communication between the chamber 72' and the water passageway 63 of the nozzle grip 56', a cavity 94 is formed on the interconnect face 91 to provide an inlet transition for the water passageway. The nozzle grip 56' is also provided with an annular O-ring groove 67 on its outer surface which is fitted with a corresponding outer O-ring 73. The outer O-ring 73 captures the nozzle nut 75 (not shown in FIG. 5b) when the nozzle grip 56' is connected to the body 11.

Returning to FIG. 6a, extending from the discharge end 61 of the nozzle grip 56 are an abrasive material extension tube 57 and a water extension tube 58. Extension tubes 57 and 58 are generally hollow cylinders which are dimensioned to be fitted within the abrasive and water mixture passageways, respectively, of the nozzle grip 56. Fitted on the opposite end of the tubes is the nozzle head 59 for directing the abrasive material stream and the water stream. The tubes are generally brazed to the nozzle grip 56 and nozzle head 59, although other means of connection may be used.

FIGS. 6b and 6c show alternate embodiments of the nozzle assembly 12' and 12" wherein the abrasive material extension tube is made removable and separately sterilizable from the nozzle assembly. In FIG. 6b, the abrasive material extension tube comprises a section of flexible tubing 94 connected at each end to a flared fitting 95, one of which is fixed in the nozzle grip 56 and the other in the nozzle head 59. The tubing 94 may be made from any suitable flexible or semi-rigid autoclavable material such as silicone or teflon. The tubing 94 is easily disconnected from the flared fittings 95 to permit easy access to the interior of the nozzle assembly 12' for cleaning and removing any clogs which may occur in the nozzle assembly. Additionally, the autoclavable material of the tubing 94 permits separate sterilization.

Alternatively, FIG. 6c shows an abrasive material extension tube 96 which has been lengthened to extend the full length of the nozzle grip 56 and to protrude beyond the rearward face 68 of the small barrel section 66. In this embodiment, the handpiece body 11 must be adapted to accommodate the protruding end 97 of the lengthened extension tube 96. The extension tube 96 is also provided with an externally threaded end 98 which engages an internal thread of the nozzle head 59. When the nozzle assembly 12" is disconnected from the handpiece body 11, the protruding end 97 of the extension tube 96 is easily manipulated to unscrew the extension tube from the nozzle head 59 and to completely remove the extension tube from the nozzle assembly.

In each of the above alternate embodiments, the nozzle head 59 includes an abrasive material discharge port 78 and a water discharge port 79 which are in fluid communication with an abrasive material inlet 80 and a water inlet 81, respectively, formed in the nozzle head. The abrasive material inlet 80 and the water inlet 81 permit fluid communication between the extension tubes 57 and 58 and their respective discharge ports 78 and 79 of the nozzle head 59. The abrasive material discharge port 78 and the water discharge port 79 are formed at an angle of approximately 120° to 130° with respect to inlets 80 and 81 and are also angled with respect to each other so that the abrasive material stream converges with the water stream at a point forward of the nozzle head. Additionally, the diameter of the air/abrasive material discharge port 78 is preferably sized larger than the diameter of the water discharge port 78 so that there is more air/abrasive flow than water from the nozzle. It has been found that a preferred ratio of discharge port diameters is roughly 2:1 and a preferred angle of convergence is roughly 10°. The larger air/abrasive discharge port 78 also helps to prevent clogging.

Referring again to FIG. 1, the nozzle grip 56 is secured to the solid body 11 by one of either a nozzle grip sleeve 74 or a nozzle grip nut 75. The nozzle grip sleeve 74 and the nozzle grip nut 75 are also preferably made from a light-weight plastic material, such as Ultem® or Radel®. The nozzle grip sleeve 74 extends substantially over the full length of the nozzle grip 56 while the nut 75 is sized to encompass only the interconnection end 60 of the grip. Both the nozzle grip sleeve 74 and the nozzle grip nut 75 are formed with internal threads to cooperatively engage the distal end external thread 53 of the body 11. Both the nozzle grip sleeve and the nozzle grip nut are also formed with an internal boss 76 which engages the shoulder flange 64 of the nozzle grip 56 to secure the nozzle assembly to the handpiece body 11 while permitting 360° rotation of the nozzle assembly relative to the handpiece body. When the sleeve 74 is used, the user grasps the outer surface of the sleeve to manipulate the tool. When the nut 75 is used, the user grasps the hexagonal outer surface of the nozzle grip 56 directly. Thus, the nozzle grip sleeve 74 and the nozzle grip nut 75 alternatively give the user the option of a wide or a narrow gripping surfaces. Furthermore, the simplicity with which the nozzle assembly 12 is connected to the body 11 facilitates easy removal and replacement with other nozzle assemblies. Where the user has more than one nozzle assembly, there can be continuous use of the instrument with one of the nozzle assemblies while the other or others are being sterilized.

Figure 8A:
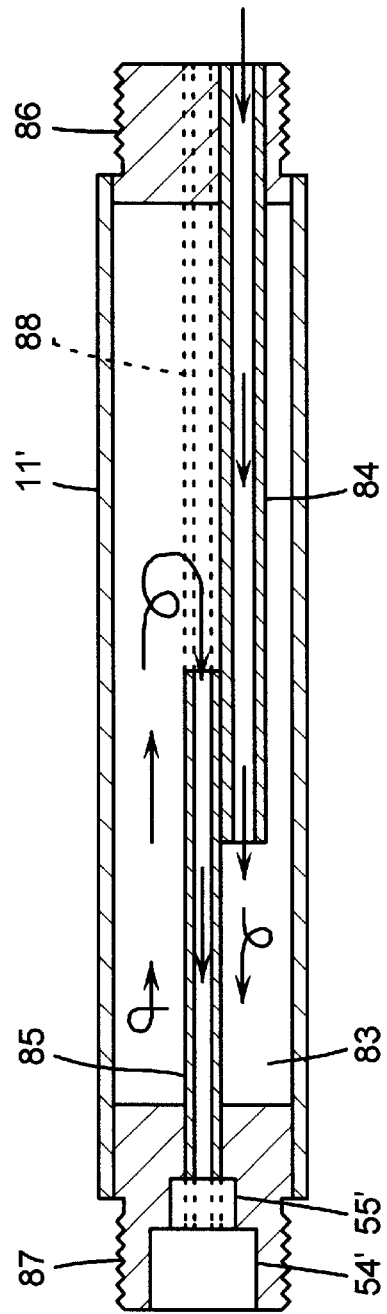
FIG. 8a is a longitudinal cross-sectional view of an alternate embodiment of the body.
Figure 8B:
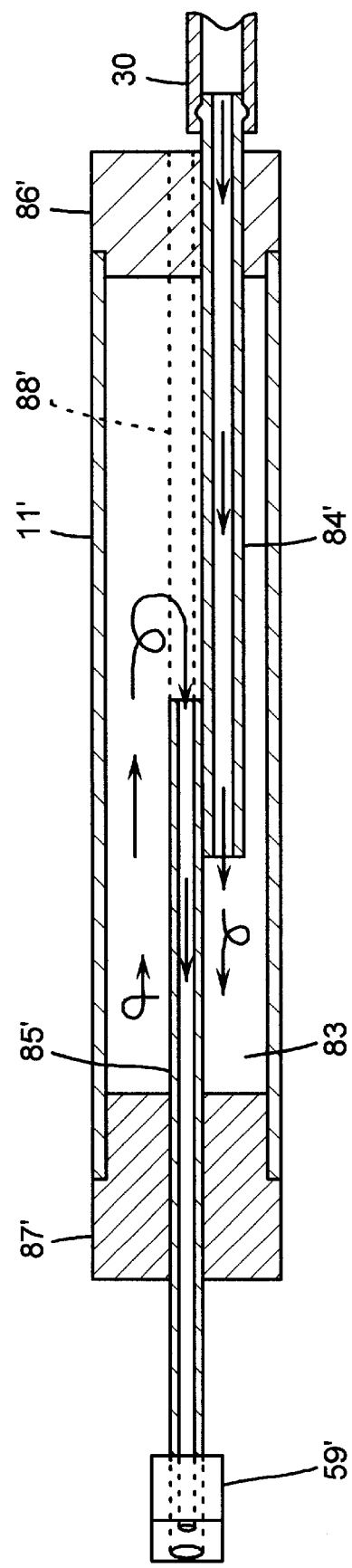
FIG. 8b is a longitudinal cross-sectional view of another alternate embodiment of the body.

As an alternative to the external abrasive material supply 13 connected to the body 11 of the instrument, the body itself may form the abrasive material supply. FIGS. 8a and 8b show an alternative embodiment wherein an abrasive material is contained within a chamber 83, defined by a body 11', into which an inlet tube 84 and an outlet tube 85 extend. The body 11' takes the form of a hollow tube having a proximal plug 86 and a distal plug 87 fixed on opposite ends thereof to seal the inner chamber 83. The body 11' and the proximal and distal plugs 86 and 87 are made from a light-weight autoclavable material, such as an Ultem® or Radel® plastic, and the body 11' is preferably transparent to allow the user to see the level of abrasive material contained within the body. Additionally, one or both of the proximal and distal plugs 86 and 87 are removable from the body 11' to permit refilling of the abrasive material. The inlet tube 84 is fixed in the proximal plug 86 and the outlet tube 85 is fixed in the distal plug 87, each tube allowing external fluid communication with the chamber 83. The body 11' is also provided with a water tube 88 extending through the body from the proximal plug 86 to the distal plug 87 which allows water to flow through the body uninterrupted. A gaseous fluid enters the chamber 83 through the inlet tube 84, agitates and becomes mixed with the abrasive material in the chamber and exits the chamber through the outlet tube 85. Preferably, the inlet and outlet tubes 84 and 85 extend past each other within the body 11' to ensure that the air entering the chamber 83 properly mixes with the abrasive material before exiting through the outlet tube.

The proximal and distal plugs 86 and 87 may be formed similar to the proximal and distal ends 19 and 20, respectively, of the body 11, i.e., having external threads, concentric counterbores in the distal plug, etc., as shown in FIG. 8a. In this case, the outlet tube 85 is in fluid communication with a small counterbore 55' of the distal plug 87 and the water tube 88 would be in fluid communication with a large counterbore 54' of the distal plug. Thus, the nozzle assembly 12 and the fluid supply line 14 would connect and operate with the body 11' exactly as described above with respect to the external abrasive material supply 13.

FIG. 8b, however, shows a further alternative embodiment in which the inlet and outlet tubes 84' and 85' extend through and beyond the proximal and distal plugs 86' and 87'. In this embodiment, the plugs 86' and 87' are formed to simply seal off the inner chamber 83 and to allow the inlet, outlet and water tubes 84', 85' and 88' to extend therethrough. At the proximal end of the body 11', the inlet tube 84' and the water tube 88' are formed with barb fittings at their external ends for connecting directly to the abrasive material and water conduits, respectively, of the fluid supply line hose 30. At the distal end, the outlet tube 85' and the water tube 88' extend beyond the distal plug 87' and are fitted with a nozzle head 59' which is identical to the nozzle head 59 described above for directing streams of the abrasive material and water to the tooth.

As a result of the present invention, a low-cost, easily manufactured dental abrading instrument is provided which is easily grasped and manipulated within the confines of a patient's mouth. The instrument is an "all-in-one" device which is connectable to an existing dental office air/water supply without the requirement for additional components and which is sterilizable by standard autoclaving techniques. The instrument also includes a fully rotatable nozzle which can be gripped comfortably between the thumb and forefinger of the user and which provides optimal mixing of a pressurized abrasive stream with a water stream outside and forward of the tip of the nozzle. A self-contained abrasive material supply is provided which is less prone to clogging due to the coaxial pick-up tube arrangement resulting in effective mixing of the abrasive material within a pressurized air stream.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention, and it is intended to claim all such changes and modifications as fall within the scope of the invention.

What is claimed is:

1. A dental instrument for directing an abrasive laden stream to a surface to be abraded comprising:

a body having a fluid inlet end for connecting to a supply of fluid and a fluid discharge end for directing a fluid to a surface to be abraded, said body including at least one passageway extending from said inlet end to said discharge end; and a supply of an abrasive material connected to said body comprising a tube arrangement in fluid communication with the at least one body passageway and a canister for holding an abrasive material, wherein said tube arrangement comprises an inner sleeve and an outer sleeve surrounding said inner sleeve, said inner sleeve having a fluid inlet conduit formed therein and said outer sleeve forming an annular fluid outlet conduit between said inner and outer sleeve, wherein a fluid enters said canister from said body through said inlet conduit, said fluid becoming mixed with said abrasive material in said canister and said fluid/abrasive material mixture is provided from said canister through said annular fluid outlet conduit to the at least one body passageway for discharge from the fluid discharge end of the body, wherein said tube arrangement has a first end and a second end, said first end being generally disposed within said canister and said second end having a cooperating coupling device for coupling said canister to said body, and wherein said cooperating coupling device includes a keyway groove, said keyway groove providing fluid communication between said annular fluid conduit and said at least one body passageway through said cooperating coupling device.

* * * * *